United States Patent [19]

Wilkerson

[11] Patent Number: 5,326,770
[45] Date of Patent: Jul. 5, 1994

[54] MONOAMINE OXIDASE-B (MAO-B) INHIBITORY 5-SUBSTITUTED 2,4-THIAZOLIDINEDIONES USEFUL IN TREATING MEMORY DISORDERS OF MAMMALS

[75] Inventor: Wendell W. Wilkerson, New Castle, Del.

[73] Assignee: The Du Pont Merck Pharmaceutical Company, Wilmington, Del.

[21] Appl. No.: 913,963

[22] Filed: Jul. 17, 1992

[51] Int. Cl.$^5$ .................. A61K 31/47; A61K 31/425; C07D 215/16; C07D 215/38; C07D 215/18; C07D 277/04

[52] U.S. Cl. .................. 514/314; 514/542; 514/369; 546/153; 546/155; 546/156; 546/157; 546/159; 546/168; 546/169; 546/170; 546/172; 546/174; 546/175; 546/178; 546/180; 546/280; 548/183; 548/181

[58] Field of Search .............. 548/181, 183; 514/369, 514/314; 546/280, 153, 155, 156, 157, 159, 168, 169, 170, 172, 174, 175, 178, 180

[56] References Cited

U.S. PATENT DOCUMENTS 3,705,153 12/1972 Kaneko et al. .................. 548/181
5,002,953 5/1991 Hindley .................. 548/181

FOREIGN PATENT DOCUMENTS 0391664 4/1989 European Pat. Off. .
0419035 8/1989 European Pat. Off. .
3077875 8/1989 Japan .
7300982 1/1972 Netherlands .

OTHER PUBLICATIONS

Gates, K. S. and Silverman, R. B., J. Am. Chem. Soc., 1990, 112:9364-9372.
Tipton, et al., Biochem. J., 1983, 209:235-242.
Dostert, et al., J. Pharm. Pharmocol., 1984, 9:585-586.
Sohda, T., et al., Chem. Pharm. Bull., 1991, 39:1440-1445.
Sohda, T., et al., Chem. Pharm. Bull., 1982, 30:3580.

*Primary Examiner*—Mary C. Lee
*Assistant Examiner*—Joseph K. McKane
*Attorney, Agent, or Firm*—Gildo R. Fato

[57] ABSTRACT

This invention relates to monoamine oxidase-B (MAO-B) inhibitory 5-substituted 2,4-thiazolidinediones, such as Formula I, to pharmaceutical compositions thereof, process of preparation, and methods of use in mammals to treat cognitive disorders, neurological dysfunction, and/or mood disturbances such as, but not limited to degenerative nervous system diseases.

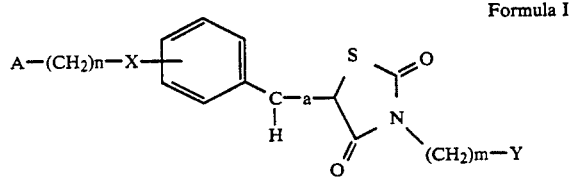

Formula I

13 Claims, No Drawings

MONOAMINE OXIDASE-B (MAO-B) INHIBITORY 5-SUBSTITUTED 2,4-THIAZOLIDINEDIONES USEFUL IN TREATING MEMORY DISORDERS OF MAMMALS

BACKGROUND OF THE INVENTION

1. Field of Invention

This invention relates to monoamine oxidase-B (MAO-B) inhibitory 5-substituted 2,4-thiazolidinediones, pharmaceutical compositions thereof, process of preparation, and methods of use in mammals to treat cognitive disorders, neurological dysfunction, and/or mood disturbances such as, but not limited to degenerative nervous system diseases.

2. Background

Increasingly there is a need for effective treatments for nervous system disorders and neurological deficiencies. Many of these diseases correlate with increasing age due mainly to degenerative changes in the nervous systems. Although in early stages of some diseases, certain systems are rather specifically affected (e.g., cholinergic systems in Alzheimer's Disease and Myasthenia Gravis, the dopaminergic system in Parkinson's Disease, etc.), multiple neurotransmitter system deficiencies (acetylcholine, dopamine, norepinephrine, serotonin) are generally found at later stages of diseases such as senile dementia, multi-infarct dementia, Huntington's Disease, mental retardation, etc. This explains the generally observed multiple symptomatology that includes cognitive, neurological, and effective/psychotic components (see Gottfries, Psychopharmacol., 86:245 (1985)).

Monoamine oxidase (MAO, EC 1.4.3.4) is an enzyme responsible for the oxidative deamination of a variety of exogenous and endogenous amines such as phenylethylamine, dopamine, serotonin, adrenaline, noradrenaline. Johnson, Biochem. Pharmacol., 17, 1285–1297 (1968) disclosed that the enzyme exist in two forms, MAO-A and MAO-B, differing in tissue distribution, structure, and substrate specificity. Some of the natural substrates for MAO-A are serotonin, octopamine, adrenaline, and noradrenaline; and some of the substrates for MAO-B are dopamine, phenylethylamine, and tyramine. MAO-B is found primarily in the platelets and the brain, and appears to increase with age. Additionally, MAO-B is significantly higher in the brains of patients with Alzheimer's Disease associated dementia (Dostert, et al., Biochem. Pharmacol., 38:555–561 (1989)). Because MAO-B is primarily responsible for the degradation of the needed neurotransmitter, dopamine, Dostert suggests that there is a rationale for the use of selective MAO-B inhibitors for the treatment of dementia and Parkinson's disease (see Strolin and Dostert in "New Directions in Effective Disorders", Eds B. Lerer and S. Gershon, Springer, New York, 262–267; and GOttfries, CG, Psychopharacol., 86:245–252 (1985)).

The most pertinent literature citations and patent references related to this invention can be found in:

Gates, KS and Silverman, RB, "5-(Aminomethyl)-3-aryl-2-oxazolidione. A Novel Class of Mechanism-Based Inactivators of Monoamine Odidase", J. Am Chem Soc., 112:9364–9372 (1990);

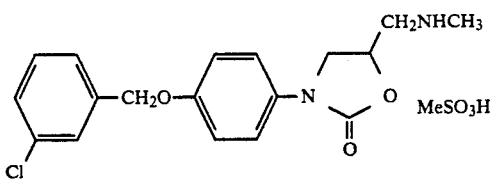

Tipton, KF, et al., "The Enzyme-Activated Irreversible Inhibition of Type-B Monoamine Oxidase by 3-{4-[(3-Chlorophenyl)methoxy]phenyl}-5-[(methylamino)-methyl]-2-Oxazolidinone Methanesulphonate (Compound MD 780236) and the Enzyme-Catalysed Oxidation of this Compound as Competing Reactions", Biochem J., 209:235–242 (1983);

Dostert, et al., "Different Stereoselective Inhibition of Monoamine Oxidase-B by the R- and S-Enantiomers of MD 780236", J. Pharm. Pharmacol., 35:161–165 (1983); Drugs of the Future, 9(8):585–586 (1984);

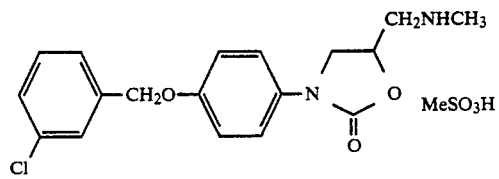

MD-780236

"New benzyl-thiazolidine-dione derivatives for prevention and treatment of hyperglycemia, diabetes II, hyperlipidemia, hypertension, cardiovascular disease, and eating disorders", Beecham Group PLC, EP 419-035-A, (Aug. 25, 1989).

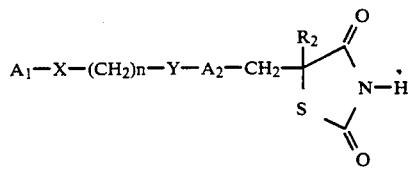

where
- $A_1$ = optionally substituted aromatic heterocyclic group;
- $A_2$ = benzene ring with up to 5 substitutions;
- X = O, S, or $NR_1$;
- $R_1$ = H, alkyl, acyl optionally substituted, aryl or optionally substituted aryl and aralkyl;
- Y = O or S;
- $R_2$ = alkyl, aralkyl, or aryl;
- n = 2 to 6

Sohda, T., et al., "Studies on Antidiabetic Agents. Synthesis and Biological Activities of Pioglitazone and Related Compounds", Chem. Pharm. Bull., 39(6):1440–1445 (1991).

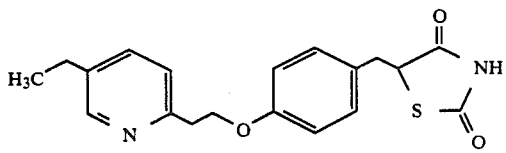

Pioglitazone

Sohda, T., et al., Chem Pharm. Bull., 30:3580 (1982).

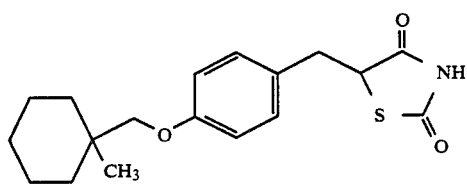

Ciglitazone

Panetta in EP 391644 disclosed 5-(4-hydroxyphenyl)-2-thioxo-4-thiazolidinones as antiinflammatories.

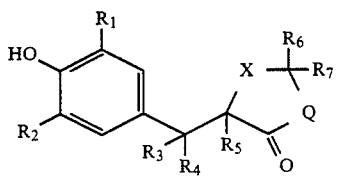

where
$R^1$, $R^2$ = H, alkyl, alkoxy, alkylcarbonyloxyalkyl;
$R^3$ = H, alkyl;
$R^4$, $R^5$ = H;
$R^4R^5$ = bond;
$R^5$, $R^6$ = H, or one of $R^6, R^7$ = H, the other = OH, SMe;
$R^5R^6$ = S, O;
$X = SO_n$;
n = 0–2.

Patent NL-7300982-Q teaches that 3-hydroxymethyl-5-benzylidene-azolidinones are anti-arthritics, anti-rheumatics, and immunosuppressants, and can be represented by the following formula:

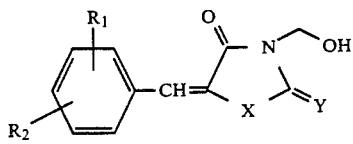

where
X = O or S;
Y = O or if X = O; may be S;
$R_1$ = H, Cl, Br, $CF_3$, CN, or $NMe_2$; and
$R_2$ = H or Cl.

Patent JA 3077-875-A described a series of 3-carboxalkyl-thiazolidine-2,4-dione derivatives as aldose reductase inhibitors for treating diabetic complications, that can be represented by the formula:

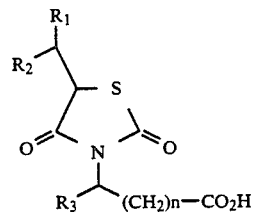

where
$R^1$ = 1–8C alkyl or 3–6C cycloalkyl;
$R^2$ = H, or 1–4C alkyl;
$R^3$ = H or 1–2C alkyl; and
n = 0–3.

None of these references teach or suggest the compounds act as MAO-B inhibitors or that they are useful for treating memory disorders.

SUMMARY OF THE INVENTION

It has been found that certain 5-substituted 2,4-thiazolidinediones improve processes involved in learning and memorization of an active avoidance task by selectively inhibiting monoamine-oxidase-B (MAO-B). Many cognitive disorders are affected by the enzyme MAO-B and these disorders can be treated by compounds which act to inhibit MAO-B. Therefore the compounds of this invention have utility in the treatment of cognitive disorders, neurological functional deficits, mood and mental disturbances in patients suffering from nervous system disorders such as, but not limited to Alzheimer's disease, Parkinson's disease, senile-dementia, multi-infarct dementia, Huntington's disease, mental retardation, and Myasthenia Gravis.

DETAIL DESCRIPTION OF THE INVENTION

This invention includes novel compounds and pharmaceutical compositions of Formula I.

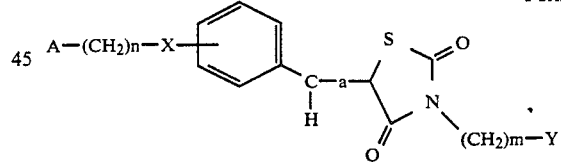

Formula I or a pharmaceutically acceptable salt thereof, wherein:
A is a straight or branched alkyl of 1 to 10 carbon atoms, phenyl optionally substituted with 1–3 substituents independently selected from the group within the definition for $R^1$, or a 5 to 10 member heterocyclic ring system including at least one nitrogen, oxygen or sulfur; optionally substituted with 1–2 substituents independently selected from the group within the definition for $R^1$;

$R^1$ is H, halo, $C_1$ to $C_{10}$ alkyl, alkenyl, alkynyl, bicycloalkyl, aryl optionally substituted with 1–2 substituents independently selected from the group within the definition for $R^2$, —C(=O)$NR^2$, —C(=O)$OR^2$, —CHO, —CN, —NO$_2$, —N(R$^2$)$_2$, $NR^2C$(=O)$R^2$, —$NR^2C$(=O)$OR^2$, —$NR^2C$(=O)$N(R^2)_2$, —$NR^2SO_2R^2$, —$OR^2$, —OC(=O)$OR^2$, —OC(=O)$N(R^2)_2$, —SO$_2N(R^2)_2$;

n is 1 to 6;

X is —CHR$^2$, —NR$^2$, O, or —S(O)p;
p is 0, 1, or 2;
a is a double bond;
m is 1 to 6;
Y is —OR$^2$, —NHR$^2$, —NR$^2$R$^3$, —CN, —COR$^2$, —CO$_2$R$^2$, —S(O)pR$^2$, or —SCN;
R$^2$ and R$^3$ are independently H, alkyl of 1 to 6 carbon atoms, aryl, acyl or alkaryl of 1 to 10 carbon atoms; with the proviso that when m is 1, then Y is not OH, and when m is 2, and Y is NR$^2$R$^3$, then R$^2$ and R$^3$ cannot simultaneously be alkyl.

Preferred compounds are those compounds of Formula I wherein:
A is a straight or branched alkyl chain of 1 to 10 carbon atoms, phenyl optionally substituted with 1-3 substituents independently selected from the group within the definition for R$^1$, pyridyl, or naphthyl;
X is O; and
Y is —CN, —COR$^2$, —CO$_2$R$^2$, —S(O)pR$^2$, or —SCN.

Most preferred compounds of Formula I are those where
A is phenyl or 2-, 3-, or 4-chlorophenyl; 2-, 3-, or 4-pyridyl;
X is O;
Y is CN, SCN, or CO$_2$R$^2$ where R$^2$ is alkyl of 1 to 4 carbon atoms.

Specifically preferred compounds of Formula I are:
a. 2,4-Dioxo-5-[3-(phenylmethoxy)-phenylmethylene]-4- thiazolidinebutanenitrile b. 2,4-Dioxo-5-[3-(phenylmethoxy)-phenylmethylene]-4-thiazolidinepentanenitrile Further included in this invention is the method of treating cognitive disorders in mammals comprising administering to the mammal a therapeutically effective amount of a compounds of formula I

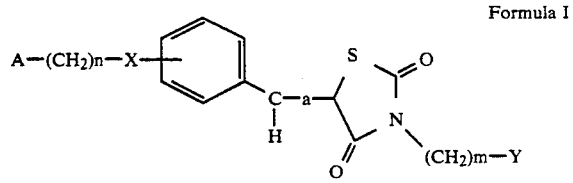

Formula I or a pharmaceutically acceptable salt thereof, wherein:
A is C$_1$ to C$_{10}$ straight or branched alkyl, alkenyl, alkynyl, cycloalkyl, cycloalkylmethyl, alkoxyalkyl, a C$_5$ to C$_{14}$ carbocyclic residue optionally substituted with 1-3 substituents independently selected from the group within the definition for R$^1$, aryl optionally substituted with 1-3 substituents independently selected from the group within the definiton for R$^1$, a 5 to 10 member heterocyclic ring system optionally including at least one nitrogen, oxygen, or sulfur; optionally substituted with 1-2 subtituents independently selected from the group within the definition for R$^1$;
R$^1$ is halo, C$_1$ to C$_{10}$ alkyl, alkenyl, alkynyl, bicycloalkyl, aryl optionally substituted with 1-2 substituents independently selected from the group within the definition for R$^2$, —C(=O)NR$^2$, —C(=O)OR$^2$, —CHO, —CN, —NO$_2$, —N(R$^2$)$_2$, —NR$^2$C(=O)R$^2$, —NR$^2$C(=O)OR$^2$, —NR$^2$C(=O)N(R$^2$)$_2$, —NR$^2$SO$_2$R$^2$, —OR$^2$, —OC(=O)OR$^2$, —OC(=O)N(R$^2$)$_2$, —SO$_2$N(R$^2$)$_2$, —S(O)R$^2$, and —SO$_2$R$^2$;
X is —CHR$^2$, —NR$^2$, O, or —S(O)p;
p is 0, 1, or 2;
a is a single or double bond;
m is 0 to 6;
Y is H, —OR$^2$, —NHR$^2$, —NR$^2$R$^3$, —CN, —COR$^2$, —CO$_2$R$^2$, —S(O)pR$^2$, or —SCN; and
R$^2$ and R$^3$ are independently H, alkyl of 1 to 6 carbons, aryl, acyl or alkaryl of 1 to 10 carbon atoms;
Preferred methods utilize those compounds of Formula I wherein:
A is a straight or branched alkyl chain of 1 to 10 carbons, phenyl optionally substituted with 1-3 substituents independently selected from the group within the definition for R$^1$, pyridyl, or naphthyl;
X is O; and
Y is H, —CN, —COR$^2$ —CO$_2$R$^2$, —S(O)pR$^2$, or —SCN, with the proviso that
a) when m is O, Y is H; and
b) when m is 1 to 6, Y is —CN, —COR$^2$, —CO$_2$R$^2$, —s(O)pR$^2$, or —SCN.

Most preferred methods utilize compounds of Formula I wherein:
A is phenyl or 2-, 3-, or 4-chlorophenyl; 2-, 3-, or 4-pyridyl;
X is O;
Y is H, —CN, —SCN, or —CO$_2$R$^2$ where R$^2$ is alkyl of 1 to 4 carbons; with the proviso that
a) when m is O, Y is H;
b) when m is 1 to 6, Y is —CN, —CO$_2$R$^2$, or —SCN.

Certain compounds of this invention may exist in geometric or stereoisomeric forms. The present invention contemplates all such compounds, including cis- and transgeometric isomers, R- and S-enantiomers, diastereomers, disomers, l-isomers, the racemic mixtures thereof, and other mixtures thereof, as falling within the scope of the invention. Additional asymmetric carbon atoms may be present in a substituent such as alkyl group. All such isomers, as well as mixtures thereof, are intended to be included in this invention.

For purposes of clarity, the terms and phrases used throughout this specification and the appended claims are defined in the following manner.

The term "alkyl" as used herein means a saturated hydrocarbon radical having from one to ten carbon atoms, which can be a straight or branched chain. Representative of such radicals are methyl, ethyl n-propyl, isopropyl, n-butyl, sec-butyl, tertiary butyl, pentyl, actyl and the like.

The term "cycloalkyl" as used herein refers to cyclic saturated aliphatic radicals containing 3 to 6 carbon atoms in the ring, such as cyclopropyl, cyclobutyl, cyclopentyl or cyclohexyl.

The term "aryl" embraces aromatic radicals such as phenyl, naphthyl and biphenyl.

The term "pharmaceutically-acceptable salts" refers to the relatively non-toxic, inorganic and organic acid addition salts of compounds of the present invention as well as the base addition salts. Representative salts include the hydrobromide hydrochloride sulfate, phosphate, and the like (see S.M. Berge et al., "Pharmaceutical Salts", J. Pharm. Sci., 66:1-19 (1977)).

The phrase "therapeutically effective amount" as used herein means an amount of a compound or composition which is an effective dose for improving processes involved in learning and memorization, or for producing some other desired therapeutic effect, at a reasonable benefit/risk ratio applicable to medical treatment.

The phrase "pharmaceutically acceptable carrier" as used herein means a pharmaceutically acceptable material or vehicle, used in a composition or formulation of a compound of this invention, suitable for use in contact with the tissues of human beings and animals without excessive toxicity, irritation, allergic response, or other problems or complications, commensurate with a reasonable benefit/risk ratio.

Most of the compounds of this invention can be synthesized by the sequence shown in Schemes 1 and Preparation C.

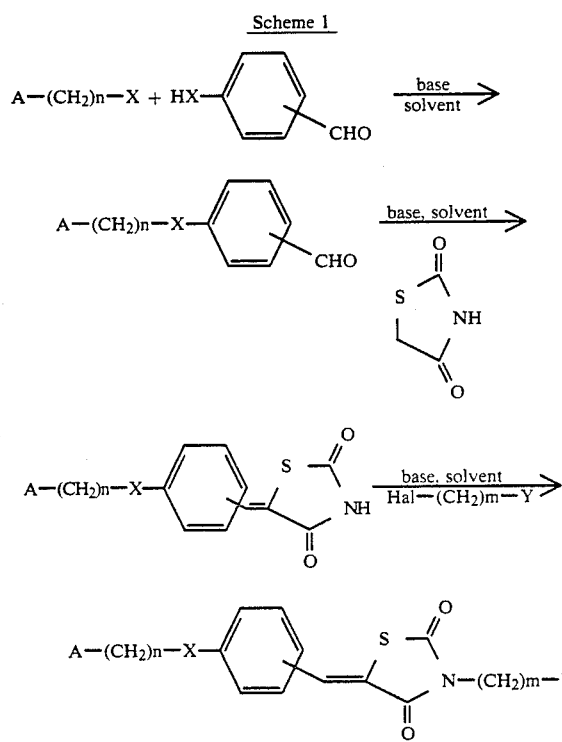

Scheme 1

The compounds of the invention and their synthesis are further illustrated by the following examples and preparations. All temperatures are in degrees Celsius.

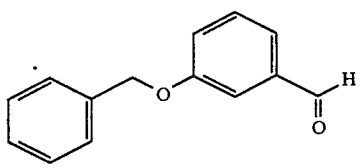

A solution of 3-hydroxybenzaldehyde (50.0 g, 409.4 mmol), benzyl chloride (51.8 g, 409.4 mmol), and $K_2CO_3$ (62.2 g, 450 mmol) in 200 ml DMF was stirred at room temperature for 48 h, filtered, and concentrated in vacuo. The residue was triturated with 500 ml water, and the resulting solid was collected by filtration, washed with water, and dried. The product was collected in 100% (87.0 g) yield; homogenous by TLC ($CHCl_3$-MeOH, 9:1); IR(melt): 1698 (CO) cm$^{-1}$; NMR ($CDCl_3$ TMS): $\delta5.15$ (s, 2H, $CH_2Ar$), [7.2 (m, 1H), 7.4 (8H), Ar], 9.95 (s, 1H, CHO).; mass spec m/e 213 (M+1).

EXAMPLE 1

5-[3-(Phenylmethoxy)phenylmethyl-ene]-2,4-thiazolidinedione

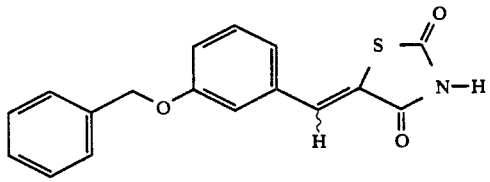

A solution of 3-benzyloxybenzaldehyde (42.45 g, 200 mmol), 2,4-thiazolidinedione (23.43 g, 200.0 mmol), and piperidine (2 g) in 150 ml pyridine was refluxed for 16 h. The mixture was concentrated in vacuo, and the residue was triturated with 500 ml hot benzene, filtered, and the filtrate left standing at room temperature for two days. The resulting crystals were collected by filtration, washed with petroleum ether, and dried to give the product in 100% yield; mp 233–235° C.; IR (nujol): 1741, 1688 (CO) cm$^{-1}$; NMR (DMSOd$_6$ TMS): $\delta5.19$ (s, 2H, ArCH$_2$), 7.15–7.25 (m, 3H), 7.3–7.5 (m, 6H), 7.73 (s, 1H, C=CH); Anal calcd for $C_{17}H_{13}NO_3$, MW 311.36: C, 65.58; H, 4.21; N, 4.50; S, 10.30. Found: C, 65.53; H, 3.91; N, 4.52; S, 10.30. Mass spec m/e 312(M+1).

EXAMPLE 2

2,4-Dioxo-5-[3-(phenylmethoxy)-phenylmethylene]-4-thiazolidinebutanenitrile

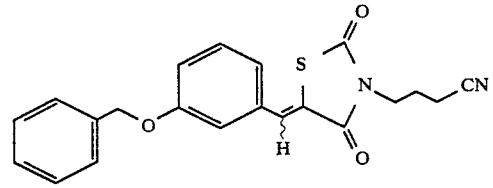

A mixture of 5-[3-(phenylmethoxy)phenylmethylene]-2,4-thiazolidinedione (10.0 g, 32.12 mmol), 4-bromobutyronitrile (5.2 g, 35.3 mmol), and $K_2CO_3$ (4.4 g, 32.12 mmol) in 100 ml THF was stirred vigorously for 16 h at room temperature. The residue was triturated with 500 ml water, and the resulting solid was collected by filtration, washed with water, and dried to give the product in 56% (6.8 g) yield; mp 137.5–138.0° C.; IR (nujol): 2237 (CN), 1729, 1675 (CO) cm$^{-1}$; NMR (DMSOd$_6$ TMS): $\delta1.90$ (m, 2H, N-C-CH$_2$), 2.57 (t, 2H, CH$_2$CN), 3.74 (t, 2H, NCH$_2$), 5.17 (s, 2H, OCH$_2$), [7.17 (s, 1H), 7.25 (s, 1H), 7.4 (m, 6H) Ar], 7.88 (s, 1H, CH=C); mass spec m/e 396(M+NH$_4$); Anal calcd for $C_{21}H_{18}N_2O_3S$, MW 378.45: C, 66.65; H, 4.79; N, 7.40; S, 8.47. Found: C, 66.53; H, 4.79; N, 7.45; S, 8.36.

When the base was changed to NaH and the solvent to dry DMF, the yield was 95%.

EXAMPLE 3

2,4-Dioxo-5-[3-(phenylmethoxy)-phenylmethylene]-4-thiazolidinepentanenitrile

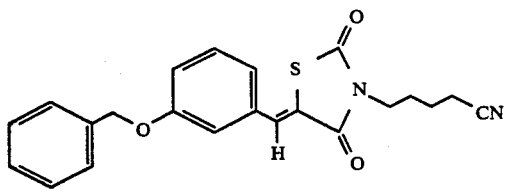

By substituting 5-valeronitrile in Example 2, the desired product was obtained in 75% (5.87 g) yield; mp 92-94° C.; IR(nujol): 2247 (CN), 1737, 1679 (CO) cm$^{-1}$; NMR(CDCl$_3$ TMS): δ1.57 (s, 1H, 0.5H$_2$O), [1.71 (m, 2H), 1.86 (m, 2H), NCCCH$_2$CH$_2$)], 2.43 (t, 2H, NC—CH$_2$), 3.81 (t, 2H, NCH$_2$), 5,12 (s, 2H, OCH$_2$), [7.1 (m, 3H), 7.4 (m, 6H) Ar], 7.86 (s, 1H, C=CH)]; mass spec m/e 393(M+1); Anal calcd for C$_{22}$H$_{20}$N$_2$O$_3$S 0.5H$_2$O, MW 401.49: C, 65.85; H, 5.27; N, 6.98; S, 7.99. Found: C, 65.72; H, 4.98; N, 6.89; S, 8.05.

PREPARATION B

Phenethyloxy-4-benzaldehyde

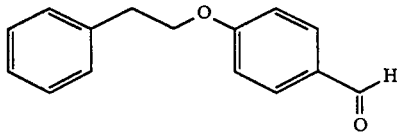

By substituting 4-hydroxybenzaldehyde and phenethyl bromine in Preparation A, the desired product was obtained as an oil in 64% yield; IR(neat): 1705 cm$^{-1}$; NMR(CDCl$_3$ TMS): δ3.08 (t, 2H, ArCH$_2$), 4.22 (t, 2H, OCH$_2$), [7.00 (d, 2H), 7.8 (d, 2H) OPhe], 7.28 (m, 5H, Phe), 11.5 (s, 1H, CHO).

EXAMPLE 4

5-[4-(2-Phenylethoxy)phenylmethylene]-2,4-thiazolidinedione

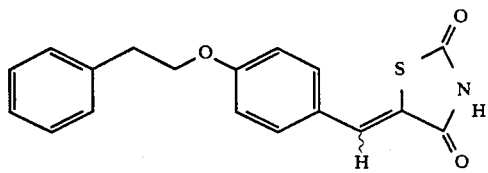

A mixture of 2,4-thiazolidinedione (3.2 g, 27.3 mmol), phenethyloxy-4-benzaldehyde (Preparation B) (6.1 g, 27.0 mmol), and piperidine (1 ml) in 50 my pyridine was refluxed for 3 h, cooled to room temperature, concentrated in vacuo, and triturated with Et$_2$O. The resulting solid was collected by filtration, washed with ether, and dried to give 9.0 g crude product. The material was triturated wi 100 ml AcOH at 70° C., cooled to room temperature, and the resulting product was collected by filtration, washed with ether, and dried to give the desired product in 46% (4.0 g) yield; mp 185-187° C.; IR(nujol): 3180 (NH), 1755 (CO), 1695 (CO) cm$^{-1}$; NMR(DMSOd$_6$ TMS): δ3.03 (t, 2H, ArCH$_2$), 4.25 (t, 2H, OCH$_2$), 7.07, 7.50 (2d, 4H, O-Ph), 7.3 (m, 5H, Ph), 7.73 (s, 1H, C=CH); mass spec m/e 325.

EXAMPLE 5

2,4-Dioxo-5-[4-(2-phenylethoxy)phenylmethylene]-3-thiazolidineacetonitrile

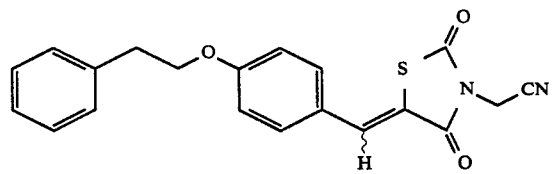

A solution of 5-[4-(2-phenylethoxy)phenylmethylene]-2,4-thiazolidinedione Example 4 (1.0 g, 3.07 mmol) in 25 ml dry DMF was treated with NaH (0.1 g, 4.2 mmol) and stirred at room temperature for 10 min. The mixture was treated with chloroacetonitrile (0.3 g, 4 mmol) and stirred at room temperature for 24 h. The mixture was poured into 500 ml ice water, and the resulting tan solid was collected by filtration, washed with water, and dried to give the desired product in 75% (1.0 g) yield; mp 155-157° C.; NMR(CDCl$_3$ TMS): δ3.13 (t, 2H, ArCH$_2$), 4.25 (t, 2H, OCH$_2$), 4.60 (s, 2H, CH$_2$CN), [7.00 (d, 2H), 7.45 (d, 2H) OPh], 7.26 (m, 5H, Ph), 7.94 (s, 1H, C=CH); Anal calcd for C$_{20}$H$_{16}$N$_2$O$_2$S, MW 364.42: C, 65.92; H, 4.43; N, 7.69; S, 8.80. Found: C, 66.15; H, 4.24; N, 7.93; S, 8.69. Mass spec m/e 365(M+1).

PREPARATION C

PREPARATION C

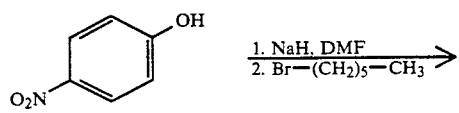

PREPARATION C

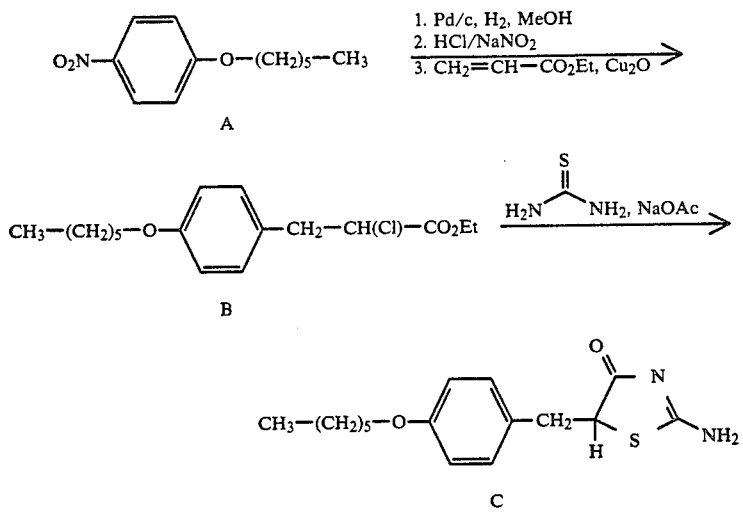

Synthesis of C1

A suspension of NaH (6.6 g, 275 xvnol) in 100 ml dry DMF was treated dropwise with a solution of 4-nitrophenol (35.0 g, 250 mmol) in 100 ml dry DMF while stirring in an ice bath for 30 min. The mixture was then treated dropwise with n-bromohexane (42.0 g, 250 mmol) in 50 ml dry DMF. The mixture was removed from the ice bath and refluxed for seven hours. The mixture was cooled to room temperature and concentrated in vacuo. The residue was partitioned between 400 ml $Et_2O$ and 200 ml 5% $NaHCO_3$. The organic layer was washed with additional 5% $NaHCO_3$, water, 1N HCl, water, and brine; dried over $MgSO_4$; filtered; and concentrated to an homogenous oil ($CHCl_3$-MeOH, 9:1) to give the desired intermediate in 98% (55.0 g) yield; NMR($CDCl_3$ TMS): δ0.93 (t, 3H, $CH_3$), 1.37 (m, 6H), 1.83 (m, 2H, O—$CCH_2$), 4.05 (t, 2H, $OCH_2$), 6.92 and 8.17 (2d, 4H, Ar); mass spec m/e 224(M+1).

Synthesis of C2: (+/−) a-Chloro-4-hexyloxy-benzenepropanoic Acid Ethyl Ester A solution of C1 (31.7 g, 142 mmol) in 200 ml MeOH under nitrogen was treated with 2g 10% Pd/c and hydrogenated at atmospheric pressure and room temperature until no starting material remained as evidenced by TLC ($CHCl_3$MeOH, 9:1). The mixture was filtered over Celite and concentrated in vacuo. The resulting oil was dissolved in 200 ml acetone, cooled in an ice bath, treated with conc. HCl (35.5 ml, 426 mmol); and treated dropwise with $NaNO_2$ (10.8 g, 156 mmol) in 25 ml water. The mixture was stirred in the ice bath for 30 min and treated with ethyl acrylate (92.3 ml, 852 mmol). The ice bath was removed, and $Cu_2O$ (0.5 g) was added in 0.1 g portions. The mixture was stirred at room temperature until the evolution of nitrogen has ceased. The mixture was concentrated in vacuo, and the residue was partitioned between 200 ml 1N HCl and 300 ml $Et_2O$. The ether layer was washed with 1N HCl and brine, dried over $MgSO_4$, filtered, and concentrated in vacuo to an impure brown oil (37.5 g). The oil was column chromatographed on silica gel (1. n-BuCl; 2. n-BuCl-$CHCl_3$, 1:1: 3. $CHCl_3$-EtOH, 9:1). Appropriate fractions were combined and concentrated to a pure oil: 66% (29.3 g) yield from C1; IR(neat): 1760 (CO) $cm^{-1}$; NMR ($CDCl_3$ TMS): δ0.90 (t, 3H, $CH_3$), 1.23 (t, 3H, $CH_3$), 1.3 (m, 6H), 1.73 (m, 2H, $CH_2$C—O), 3.0–3.4 (m, 2H, $ArCH_2$), 3.92 (t, 2H, $OCH_2$), 4.17 (g, 2H, $OCH_2$), 4.37 (t, 1H, Cl—CH), 6.82 and 7.12 (2d, 4H, Ar); mass spec m/e 313(M+1).

Synthesis of C3: (+/−) 2-Amino-5-[4-hexyloxy-phenyl(methyl)]-thiazol-4-[5]-one A mixture of C2 (17.0 g, 54.3 mmol), thiourea (6.62 g, 86.9 mmol), and sodium acetate (4.45 g, 54.2 mmol) in 110 ml methoxyethanol was refluxed for 16 h. The mixture was concentrated in vacuo, and the residue triturated with a mixture of 50 ml hexanes and 50 ml water, and filtered. The result was a solid, orange colored organic phase, and an aqueous phase. The crude product (solid) was recrystallized from hot ethanol to give the desired product in 49% (8.1 g) yield; mp 219–221° C.; IR(nujol): 3250 (NH), 1680 (CO) $cm^{-1}$; NMR($DMSOd_6$ TMS): δ0.87 (t, 3H, $CH_3$), 1.30 (m, 6H), 3.3 (dd, 2H, $ArCH_2$), 3.90 (t, 2H, $OCH_2$), 4.53 (dd, 1H, SCH), 6.80 and 7.12 (2d, 4H, Ar), [8.67 (s, 1H), 8.90 (s, 1H) $NH_2$]; mass spec m/e 307(M+1).

EXAMPLE 6

5-[(4-Hexyloxyphenyl)methyl]-2,4-thiazolidinedione

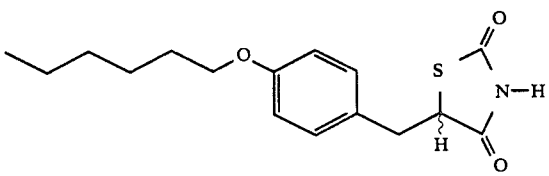

A mixture of (+/−) 2-Amino-5-[4-hexyloxyphenyl(methyl)]-thiazol-4-[5]-one (C3) (5.0 g, 16.32 mmol) and 2N HCl (10 ml, 20 meq) in 50 ml 2-methoxyethanol was refluxed for four hours, and concentrated to an oil. The mixture was partitioned between 100 ml water and 200 ml Et₂O, and the organic phase was washed with water and brine, dried over MgSO₄, filtered, and concentrated. The oily residue was recrystallized from hexanes to give the product in 100% (5.0 g) yield; mp 52–54° C.; IR(neat): 3240 (NH), 1770, 1715 (CO) cm⁻¹; NMR(CDCl₃ TMS): δ0.9 (t, 3H, CH₃), 1.33 (m, 6H), [3.1 (m, 1H), 3.46 (dd, 1H), ArCH₂], 3.92 (t, 2H, OCH₂), 4.5 (dd, 1H, SCH), 6.82 and 7.12 (2d, 4H, Ar), 9.07 (s, 1H, NH); mass spec 308(M+1).

EXAMPLE 7

5-[4-(3-Adamantylmethoxy)phenylmethyl]-2,4-thiazolidinedione

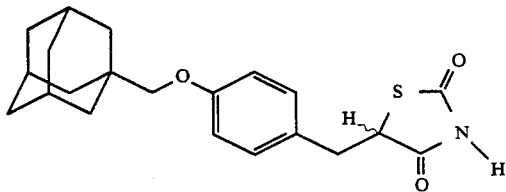

By substituting 1-adamantane methanol in Preparation C, followed by the procedure in Example 6, the desired product was obtained in 92% at the hydrolysis step and 41% overall yield; mp 188–191° C.; IR(nujol): 3200 (NH), 1760, 1700 (CO) cm⁻¹; NMR(DMSOd₆ TMS): δ1.5–2.0 (m, 15H, Adm), 3.07, 3.3 (2m, 2H, ArCH₂), 3.50 (s, 2H, OCH₂), 4.87 (m, 1H, S—CH), 6.87, 7.13 (2d, 4H, Ar), 12.03 (s, 1H, NH); mass spec m/e 371.

EXAMPLE 8

5-{4-[(3-Chlorophenyl)methoxy]phenylmethylene}-2,4-thiazolidinedione

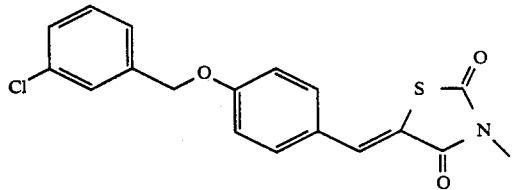

By substituting 3-chlorobenzyl bromide in Preparation B followed by the procedure in Example 4, the desired product was obtained in 46% yield after recrystallization from benzene; mp 182–183° C.; IR(nujol): 1742, 1697 (CO) cm⁻¹; NMR(DMSOd₆ TMS: δ5.21(s, 2H, OCH₂), [7.18 (d, 2H), 7.57 (d, 2H), 1,4-Ph], [7.43 (m, 3H), 7.54 (s, 1H), 1,3-Ph], 7.75 (s, 1H, C=CH), 12.5 (broad s, 1H, NH); Anal calcd C₁₇H₁₂NO₃SCl, MW 345.80: C, 59.05; H, 3.50; N, 4.05; S, 9.27. Found: C, 58.90; H, 3.78; N, 4.01; S, 9.42. Mass spec m/e 346 (M+1).

EXAMPLE 9

5-{4-[(3-Chlorophenyl)methoxy]phenylmethylene{-2,4-thiazolidinebutanenitrile

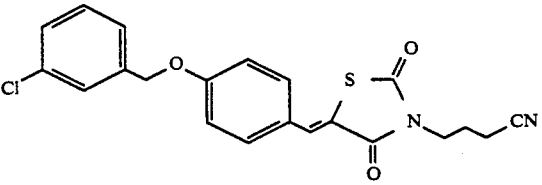

By substituting the product from Example 8 in the procedure for Example 5, the desired product was obtained in 82% yield; mp 157–158° C.; IR(nujol): 2244 (CN), 1726, 1680 cm⁻¹; NMR(DMSOd₆ TMS): δ1.89 (m, 2H, CH₂CCN), 2.57 (t, 2H, CH₂CN), 3.73 (t,2H, NCH₂), 5.22 (s, 2H, OCH₂), [7.20 (d, 2H), 7.61 (d, 2H), 1,4-Ph], [7.44 (m, 3H), 7.54 (s, 1H), 1,3-Ph]. 7.89 (s, 1H, C=CH). Anal calcd for C₂₁H₁₇N₂O₃SCl, MW 412.89: C, 61.09; H, 4.15; N, 6.78; S, 7.77. Found: C, 60.89; H, 4.04; N, 6.64; S, 7.69. Mass spec m/e 413 (M+1).

By using the methods in the examples above, the following compounds of this invention can be synthesized:

TABLE I

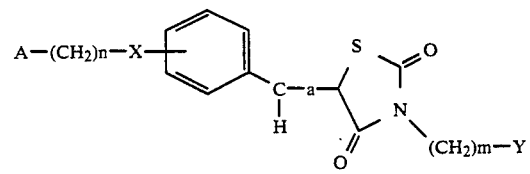

| Ex | A | n | X | a | m | Y |
|----|---|---|---|---|---|---|
| 10 | Ph | 1 | 3-O | CH=C | 1 | CN |
| 11 | Ph | 1 | 3-O | CH=C | 2 | CN |
| 12 | Ph | 1 | 3-O | CH=C | 5 | CN |
| 13 | Ph | 1 | 3-O | CH=C | 6 | CN |
| 14 | Ph | 1 | 3-O | CH=C | 1 | CO₂Et |
| 15 | Ph | 1 | 3-O | CH=C | 2 | CO₂Et |
| 16 | Ph | 1 | 3-O | CH=C | 3 | CO₂Et |
| 17 | Ph | 1 | 3-O | CH=C | 4 | CO₂Et |
| 18 | Ph | 1 | 3-O | CH=C | 5 | CO₂Et |
| 19 | Ph | 1 | 3-O | CH=C | 6 | CO₂Et |
| 20 | Ph | 1 | 3-S | CH=C | 3 | CN |
| 21 | Ph | 1 | 3-SO₂ | CH=C | 3 | CN |
| 22 | Ph | 1 | 3-SO | CH=C | 3 | CN |
| 23 | Ph | 1 | 3-N—CH₃ | CH=C | 3 | CN |
| 24 | Ph | 1 | 3-O | CH=C | 2 | SCN |
| 25 | Ph | 1 | 3-O | CH=C | 3 | SCN |
| 26 | Ph | 1 | 3-O | CH=C | 4 | SCN |
| 27 | Ph | 1 | 3-O | CH=C | 3 | NHCH₃ |
| 28 | Ph | 1 | 3-O | CH=C | 3 | N(CH₃)₂ |
| 30 | 2-Cl—Ph | 1 | 3-O | CH=C | 3 | CN |
| 31 | 3-Cl—Ph | 1 | 3-O | CH=C | 3 | CN |
| 32 | 4-Cl—Ph | 1 | 3-O | CH=C | 3 | CN |
| 33 | Ph | 2 | 4-O | CH=C | 0 | CN |
| 34 | Ph | 3 | 4-O | CH=C | 3 | CN |
| 35 | Ph | 4 | 4-O | CH=C | 3 | CN |
| 36 | Ph | 5 | 4-O | CH=C | 3 | CN |
| 37 | Ph | 6 | 4-O | CH=C | 3 | CN |
| 38 | Ph | 1 | 3-CH₂ | CH=C | 3 | CN |

BIOCHEMICAL TEST PROCEDURE

Monoamine oxidase- B (MAO-B) and A (MAO-A) Assays

The inhibitory activities of the compounds of this invention and that of the standard deprenyl were determined using the method described and incorporated by reference by Fowler and Benedetti, "The Metabolism of Dopamine by Both Forms of Monoamine Oxidase in the Rat Brain and its Inhibition by Cimoxatone", J. Neurochemistry, 40(6):1534–1541 (1983).

TABLE II

| Example number | Monoamine oxidase inhibition | | | AMPT $ED_{50}$ mg/kg |
|---|---|---|---|---|
| | MAO-B $IC_{50}$ mM | MAO-A $IC_{50}$ mM | Ratio A/B | |
| 1 | 100.0 | 100.0 | 1 | |
| 2 | 0.1 | >5000.0 | >50000 | |
| 3 | 0.7 | >1000.0 | >1428 | |
| 4 | 0.1 | 30.0 | >300 | |
| 5 | 2.0 | 30.0 | 15 | |
| 6 | 0.1 | 10.0 | 100 | 6.71 |
| 7 | 0.1 | 30.0 | 300 | |
| 8 | 30.0 | >100.0 | >3 | |
| 9 | 100.0 | 30.0 | <1 | |
| Deprenyl | 0.0035 | >1000.0 | >280000 | |

Utility

The foregoing test results suggest that the compounds of this invention have utility in the treatment of cognitive disorders and/or neurological function deficits and/or mood and mental disturbances in patients suffering from nervous system disorders like Alzheimer's disease, Parkinson's disease, senile-dementia, multi-infarct dementia, Huntington's disease, mental retardation, Myasthenia Gravis, etc. Compounds of this invention can be administered to treat said deficiencies by any means that produces contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition, The active ingredient can be administered orally in solid dosage forms, such as capsules, tablets, and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference ion this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil was prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed absorption.

The compounds of this invention may also be used as reagents or standards in the biochemical study of neurological function, dysfunction, and/or disease.

What is claimed is:

1. A compound of the Formula

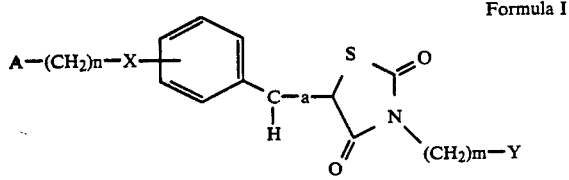

Formula I or a pharmaceutically acceptable salt thereof, wherein:
A is a straight or branched alkyl of 1 to 10 carbon atoms, phenyl optionally substituted with 1-3 substituents independently selected from the group within the definition for $R^1$, pyridyl or naphythyl
$R^1$ is H, halo, $C_1$ to $C_{10}$ alkyl, alkenyl, alkynyl, bicycloalkyl, aryl optionally substituted with 1-2 substituents independently selected from the group within the definition for $R^2$, $-C(=O)NR^2$, $-C(=O)OR^2$, $-CHO$, $-CN$, $-NO_2$, $-N(R^2)_2$, $NR^2C(=O)R^2$, $-NR^2C(=O)OR^2$, $-NR^2C(=O)N(R^2)_2$, $-NR^2SO_2R^2$, $-OR^2$, $-OC(=O)OR^2$, $-OC(=O)N(R^2)_2$, $-SO_2N(R^2)_2$, $-S(O)R^2$, and $-SO_2R^2$;
n is 1 to 6;
X is O, S(O)p, or $NCH_3$
p is 0, 1, or 2;
a is a double bond;
m is 1 to 6
Y is $-CN$, $-COR^2$, $-CO_2R^2$, $-S(O)pR^2$, or $-SCN$;
$R^2$ and $R^3$ are independently H, alkyl of 1 to 6 carbon atoms, aryl, acyl or alkaryl of 1 to 10 carbons.

2. A compound of claim 1
A is phenyl or 2-, 3-, or 4-chlorophenyl; 2-, 3-, or 4-pyridyl;
X is O;
Y is Cn, SCN, or $CO_2R^2$; where $R^2$ is alkyl of 1 to 4 carbons.

3. A compound of claim 1 wherein
A is phenyl or 2, 3 or 4 chlorophenyl;
n is 1 or 2;
X is O;
m is 1, 3 or 4; and
Y is H or CN.

4. The compound of claim 1 which is 2,4-Dioxo-5-[3-(phenylmethoxy)-phenylmethylene]-4-thiazolidinebutanenitrile.

5. The compound of claim 1 which is 2,4-Dioxo-5-[3-(phenylmethoxy)-phenylmethylene]-4-thiazolidinepentanenitrile.

6. A pharmaceutical composition comprising a monoamine oxidase B inhibitory effective amount of a compound of claim 1 and a pharmaceutically acceptable carrier.

7. A pharmaceutical composition comprising a monoamine oxidase B inhibitory effective amount of a compound of claim 2 and a pharmaceutically acceptable carrier.

8. A pharmaceutical composition comprising a monoamine oxidase B inhibitory effective amount of a compound of claim 3 and a pharmaceutically acceptable carrier.

9. A pharmaceutical composition comprising a monoamine oxidase B inhibitory effective amount of a compound of claim 4 and a pharmaceutically acceptable carrier.

10. A pharmaceutical composition comprising a monoamine oxidase B inhibitory effective amount of a compound of claim 5 and a pharmaceutically acceptable carrier.

11. A method of treating cognitive disorders in mammals suffering from a nervous system disorder selected from the group consisting essentially of Alzheimer's disease, senile dementia, multi-infarct dementia, or mental retardation, comprising administering to the mammal in need of such treatment a therapeutically effective amount of a compounds of formula I

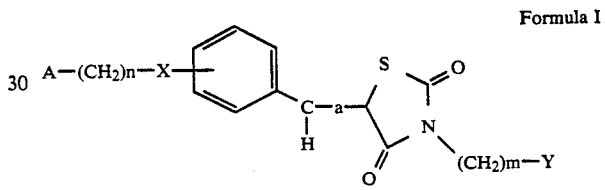

Formula I or a pharmaceutically acceptable salt thereof, wherein:
A is $C_1$ to $C_{10}$ straight or branched alkyl, alkenyl, alkynyl, cycloalkyl, cycloalkylmethyl, alkoxyalkyl; a $C_5$ to $C_{14}$ carbocyclic residue optionally substituted with 1-3 substituents independently selected from the group within the definition for $R^1$, aryl optionally substituted with 1-3 substituents independently selected from the group within the definition for $R^1$; or pyridyl, naphthyl or quinolinyl optionally substituted with 1-2 substituents independently selected from the group within the definition for $R^1$;
$R^1$ is halo, $C_1$ to $C_{10}$ alkyl, alkenyl, alkynyl, bicycloalkyl, aryl optionally substituted with 1-2 substituents independently selected from the group within the definition for $R^2$, $-C(=O)NR^2$, $-C(=O)OR^2$, $-CHO$, $-CN$, $-NO_2$, $-N(R^2)_2$, $-NR^2C(=O)R^2$, $-NR^2C(=O)OR^2$, $-NR^2C(=O)N(R^2)_2$, $-NR^2SO_2R^2$, $-OR^2$, $-OC(=O)OR^2$, $-OC(=O)N(R^2)_2-SO_2N(R^2)_2$, $-S(O)R^2$, and $-SO_2R^2$;
X is $-CHR^2$, $-NR^2$, O, or $-S(O)p$;
p is 0, 1, or 2;
a is a single or double bond;
m is 0 to 6;
Y is H, $-OR^2$, $-NHR^2$, $-NR^2R^3$, $-CN$, $-COR^2$, $-CO_2R^2$, $-S(O)pR^2$, or $-SCN$; and
$R^2$ and $R^3$ are independently H, alkyl of 1 to 6 carbons, aryl, acyl or alkaryl of 1 to 10 carbon atoms.

12. The method of claim 11

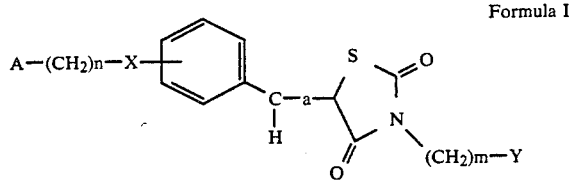

Formula I or a pharmaceutically acceptable salt thereof, wherein:
A is a straight or branched alkyl chain of 1 to 10 carbons, phenyl optionally substituted with 1-3 substituents independently selected from the group within the definition for $R^1$, pyridyl, or naphthyl;
$R^1$ is halo, $C_1$ to $C_{10}$ alkyl, alkenyl, alkynyl, bicycloalkyl, aryl optionally substituted with 1-2 substituents independently selected from the group within the definition for $R^2$, —C(=O)$NR^2$, —C(=O)$OR^2$, —CHO, —CN, —NO$_2$, —N($R^2$)$_2$, —$NR^2$C(=O)$R^2$, —$NR^2$C(=O)$OR^2$, —$NR^2$C(=O)N($R^2$)$_2$, —$NR^2$SO$_2R^2$, —$OR^2$ —OC(=O)$OR^2$, —OC(=O)N($R^2$)$_2$, —SO$_2$N($R^2$)$_2$, —S(O)$R^2$, and —SO$_2R^2$;
X is O,;
p is 0, 1, and 2;
a is a single or double bond;
m is 0 to 6;
Y is H, —Cn, —COR$^2$ —CO$_2R^2$, —S(O)p$R^2$, or —SCN, with the proviso that
a) when m is O, Y is H; and
b) when m is 1 to 6, Y is —Cn, —COR$^2$, —CO$_2R^2$, —S(O)p$R^2$, or —SCN; and
$R^2$ and $R^3$ are independently H, alkyl of 1 to 6 carbons, aryl, acyl or alkaryl of 1 to 10 carbon atoms.

13. The method of claim 12 wherein:
A is phenyl or 2-, 3-, or 4-chlorophenyl; 2-, 3-, or 4-pyridyl,
X is O,
Y is H, —CN, —SCN, or —CO$_2R^2$, where $R^2$ is alkyl of 1 to 4 carbons with the proviso that
a) when m is O, Y is H; and
b) when m is 1 to 6, Y is —Cn, —CO$_2R^2$, or —SCN.

* * * * *